(12) United States Patent
Frigg et al.

(10) Patent No.: US 6,855,146 B2
(45) Date of Patent: Feb. 15, 2005

(54) INTRAMEDULLARY NAIL

(76) Inventors: Robert Frigg, Mattenweg 8, Bettlach (CH), 2544; Peter Brunner, Effingerstrasse 93, Bern (CH), 3008

( * ) Notice: Subject to any disclaimer, the term of this patent is extended or adjusted under 35 U.S.C. 154(b) by 274 days.

(21) Appl. No.: 10/158,874

(22) Filed: Jun. 3, 2002

(65) Prior Publication Data
US 2003/0004514 A1 Jan. 2, 2003

Related U.S. Application Data

(63) Continuation of application No. PCT/CH99/00581, filed on Dec. 3, 1999.

(51) Int. Cl.[7] .............................................. A61B 17/72
(52) U.S. Cl. ......................................... 606/64; 606/65
(58) Field of Search .............................. 606/62, 63, 64, 606/65, 66, 67

(56) References Cited

U.S. PATENT DOCUMENTS

| | | |
|---|---|---|
| 3,433,220 A | 3/1969 | Zickel |
| 4,622,959 A | 11/1986 | Marcus |
| 4,827,917 A | 5/1989 | Brumfield |
| 5,167,663 A | 12/1992 | Brumfield |
| 5,312,406 A | 5/1994 | Brumfield |
| 5,549,610 A | 8/1996 | Russell et al. |
| 6,120,504 A | 9/2000 | Brumback et al. |
| 6,168,595 B1 | 1/2001 | Durham et al. |
| 6,210,414 B1 | 4/2001 | Lin |
| 6,402,753 B1 | 6/2002 | Cole et al. |
| 6,461,360 B1 | 10/2002 | Adam |
| 6,569,165 B2 | 5/2003 | Wahl et al. |
| 6,579,294 B2 | 6/2003 | Robioneck |
| 6,652,528 B2 | 11/2003 | Vandewalle |

FOREIGN PATENT DOCUMENTS

| | | |
|---|---|---|
| EP | 0 551 588 A1 | 7/1993 |
| GB | 2209947 A | 6/1989 |

*Primary Examiner*—David O. Reip
(74) *Attorney, Agent, or Firm*—Jones Day

(57) ABSTRACT

The invention relates to an intramedullary nail used for treating fractures of the femur. It comprises a distal end, which is appointed for insertion into the marrow cavity channel, a proximal end, and a longitudinal axis. A first bore is located adjacent the proximal end and extends through the proximal end and transversely intersects the longitudinal axis, and serves to accommodate a femoral head screw. The center axis of the first bore forms an angle with the longitudinal axis that ranges from 110° to 150°. A second bore is located between the first bore and the proximal end and extends through the proximal end and transversely intersects the longitudinal axis, and serves to accommodate a hip pin. The second bore is at least partially shaped as an oblong hole or slot with a width B and a length L>B, and the length L of the oblong hole extends in the direction of the longitudinal axis.

19 Claims, 5 Drawing Sheets

INTRAMEDULLARY NAIL

CROSS-REFERENCE TO RELATED APPLICATIONS

This application is a continuation of the U.S. national stage designation of copending International Patent Application PCT/CH99/00581, filed Dec. 3, 1999, the entire content of which is expressly incorporated herein by reference thereto.

FIELD OF THE INVENTION

The present invention relates generally to an intramedullary nail

BACKGROUND OF THE INVENTION

An intramedullary pin of this type has been described in EP-A 0 551 588. Its particular shortcomings consist of the fact that the two hip screws which are inserted in the head of the femur (femur-head screw and hip pin) extend through the circular openings in the intramedullary fastening pin in angularly rigid fashion. Due to their dimensionally defined difference in flexural strength it is possible during the clinical process for these two screws to move relative to each other. The smaller hip pin, because of its limited or even inhibited gliding ability, can penetrate the hip joint.

SUMMARY OF THE INVENTION

The present invention is directed to an intramedullary nail for the treatment of femoral fractures, comprising a distal end for insertion in the medullary channel, a proximal end, a longitudinal axis, and defining a first borehole located adjacent the proximal end extending through the proximal end and horizontally intersecting the longitudinal axis. The first borehole is configured to accept a femoral head screw and defines a center line extending at an angle of between about 30° to 70° relative to the longitudinal axis. A second borehole is positioned between the first borehole and the proximal end and extends through the proximal end and horizontally intersects the longitudinal axis. The second borehole is configured to accept a hip pin and is at least in part elongated into a slot having a width B and a length L>B, with the length L of the slot extending in the direction of the longitudinal axis.

The fact that the slot-shaped, elongated hole eliminates the angular rigidity in the direction of the longitudinal axis of the hip pin presents no drawback compared to prior art, since any rotation of the femoral head around the femoral-head screw remains inhibited by the hip pin which, after all, is and always will be the purpose of the hip pin. The use of an elongated hole for accepting the hip pin offers an advantage insofar as it permits mechanical load distribution of the two hip screws. The larger one of the femoral head screws performs the function of ensuring angular rigidity of the screw anchored in the femoral head relative to the intramedullary fastening pin while permitting a "sintering" of the femoral head fragment through axial movement in the corresponding intramedullary fastening pin borehole. The smaller hip pin merely serves to secure the femoral head rotationally relative to the larger femoral bead screw.

In a preferred form of implementation of this invention, the first borehole is cylindrically round. Preferably, the lateral entry opening of the second borehole is cylindrically round while the medial exit opening of the second borehole is preferably elongated into a slot.

In another implementation both the lateral entry opening and the medial exit opening of the second borehole may be slot-shaped.

The width B of the second borehole is preferably smaller than the diameter D of the first borehole.

The center line of the first borehole preferably extends at an angle $\alpha$ of 40°–55° relative to the longitudinal axis. The center line of the second borehole preferably extends at an angle $\beta$ of 30° to 70° relative to the longitudinal axis or an angle 180°–$\beta$ from 110° to 150°. This is the preferred position for a non-moving anchoring screw. The angle $\beta$ may equally well have a value of 70° to 90° for as long as the angle $\alpha$ is within the same angular range. This is the preferred position for a moving hip screw. The length L of the elongated hole or slot is preferably 8 to 12 mm and typically 9 to 11 mm. The width B of the elongated hole is preferably 5 to 10 mm and typically 6 to 7 mm. The L:B ratio is preferably in the range from 1.05 to 2.00 and typically 1.10 to 1.60.

A preferred implementation additionally includes at least one third borehole near the distal end horizontally intersecting the longitudinal axis and serving to accept a distal locking screw.

In another implementation the lateral entry opening of the second borehole may be slot-shaped while the medial exit opening of that second borehole is cylindrically round.

The hip pin to be used as part of a fixation system in conjunction with the intramedullary fastening pin should preferably be 5 to 20 mm and typically 10 to 15 mm shorter than the femoral head screw employed. The diameter of the hip pin should preferably correspond to the width B of the slot-shaped second borehole.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
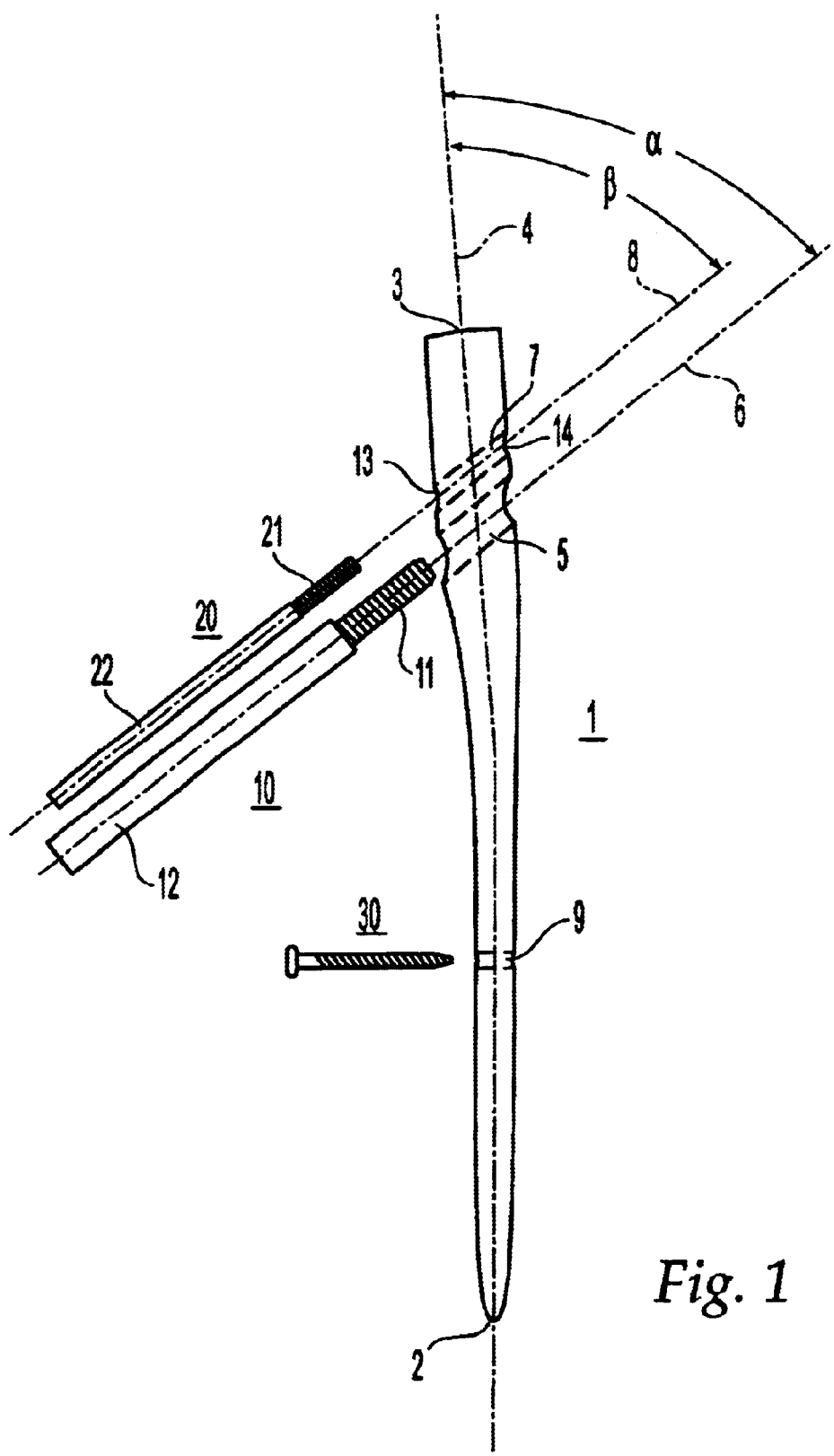
FIG. 1 is a longitudinal cut-away view through the intramedullary fastening pin according to this invention and, in an exploded view, the matching hip and locking screws.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

The intramedullary nail or intramedullary fastening pin 1 illustrated in FIG. 1, serving to stabilize femoral fractures, includes a distal end 2 intended for insertion in the medullary channel, a proximal end 3 and a longitudinal axis 4. Closer to its proximal end 3 and intersecting the longitudinal axis 4, the fastening pin 1 is provided with a first borehole 5, having a longitudinal axis or center line 6, designed to accept a hip screw 10. The center line 6 of the first cylindrically round borehole 5 extends at an angle α of 30° to 70° relative to the longitudinal axis 4, or an angle 180°-α of 110° to 150°. Additionally, the fastening pin 1 is provided between the first borehole 5 and the proximal end 3 with a second borehole 7, having a center line 8, horizontally intersecting the longitudinal axis 4 and serving to accept a hip pin 20. The center line of the second borehole extends at an angle β of 45° relative to the longitudinal axis.

Figure 2:
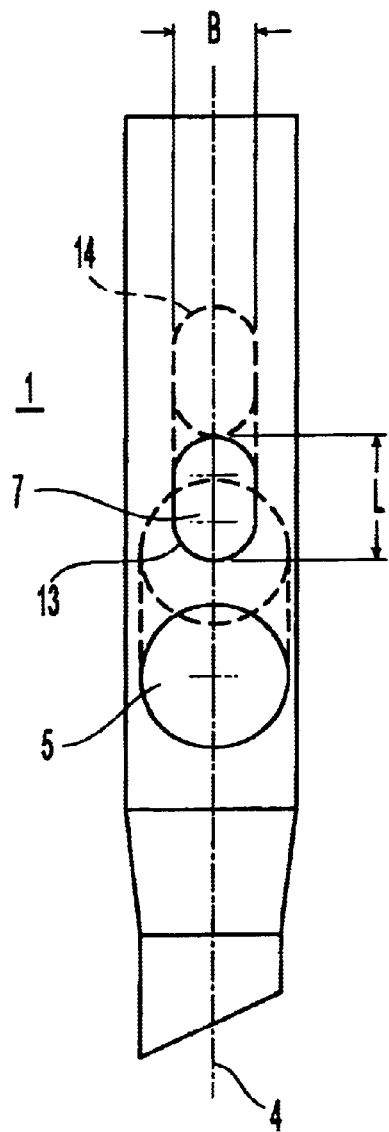
FIG. 2 is a view, rotated 90°, of the proximal section of the fastening pin shown in FIG. 1.

As depicted in FIG. 2, both the lateral entry opening 13 and the medial exit opening 14 of the second borehole 7 are elongated slots. This design makes it possible for the hip pin 20 that is inserted in the borehole 7 in the lateromedial plane (corresponding to the plane of projection in FIG. 1) to be slightly angled in both directions, i.e. up and down, relative to the axis 8.

Figure 3:
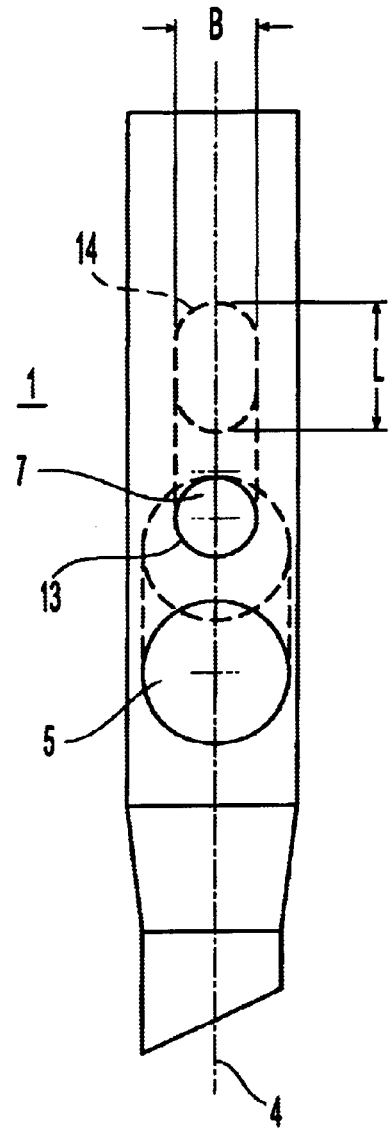
FIG. 3 shows a modified proximal section of the fastening pin according to FIG. 1.
Figure 9:
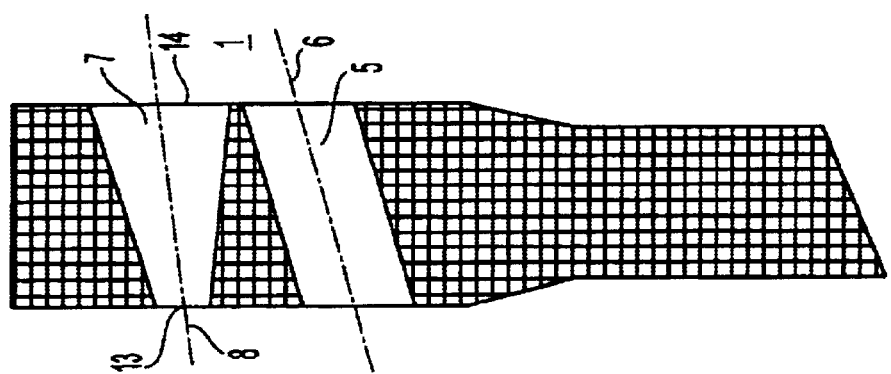
FIG. 9 is a cut-away view through a proximal section of an intramedullary fastening pin with a lateromedially widening slot.
Figure 8:
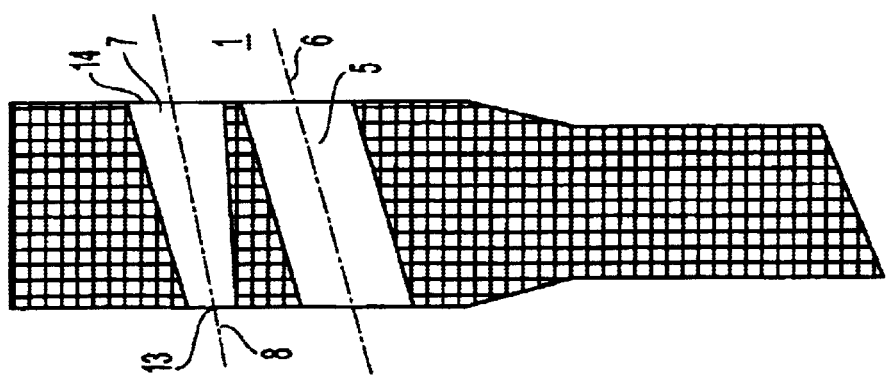
FIG. 8 is a cut-away view through the proximal section according to FIG. 3 with a lateromedially flared slot sloping toward the proximal end.

As shown in FIG. 3 (as well as in FIGS. 8 and 9), the second borehole 7 may also be shaped in a way that its lateral entry opening 13 is cylindrically round while its medial exit opening 14 is slot-shaped. In that case the hip pin 20 inserted in the borehole 7 will be fully enclosed at the lateral entry opening 13, permitting limited movement only in the lateromedial plane (corresponding to the plane of projection in FIG. 1) relative to the axis 8.

Figure 6:
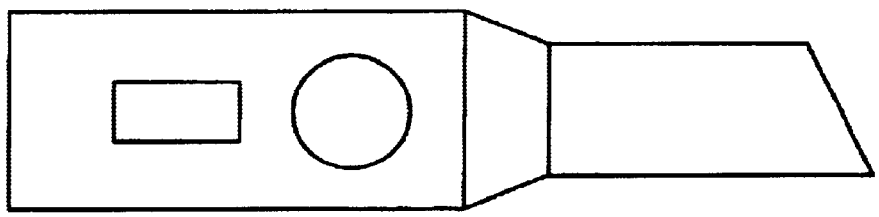
FIG. 6 is a lateral view of the proximal section of the intramedullary fastening pin, with a rectangular slot.
Figure 5:
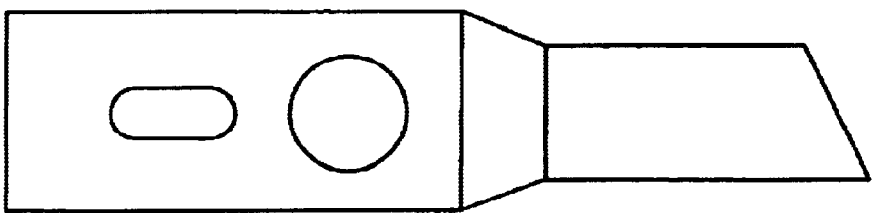
FIG. 5 is a lateral view of the proximal section of the fastening pin with a substantially rounded slot.
Figure 10:
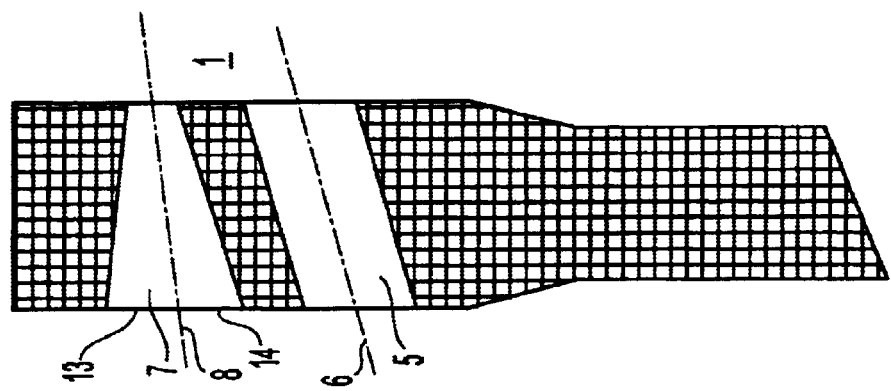
FIG. 10 is a cut-away view through a proximal section of an intramedullary fastening pin with a lateromedially narrowing slot.

As shown in FIGS. 2, 3, 5 and 7, the elongated hole may have rounded corners (produced by drilling the hole with a round drill bit or cutter and moving the latter in a direction perpendicular to the tool axis), or, as shown in FIG. 6, it may be rectangular with squared corners. Whether rounded or rectangular, the slot has the same width B and a length L>B, with the length L of the slot extending in the direction of the longitudinal axis 4. The width B of the second borehole 7 is preferably smaller than the diameter D of the first borehole 5. The slot length is 10 mm, its width 6.5 mm, corresponding to a L:B ratio of 1.538.

Figure 4:
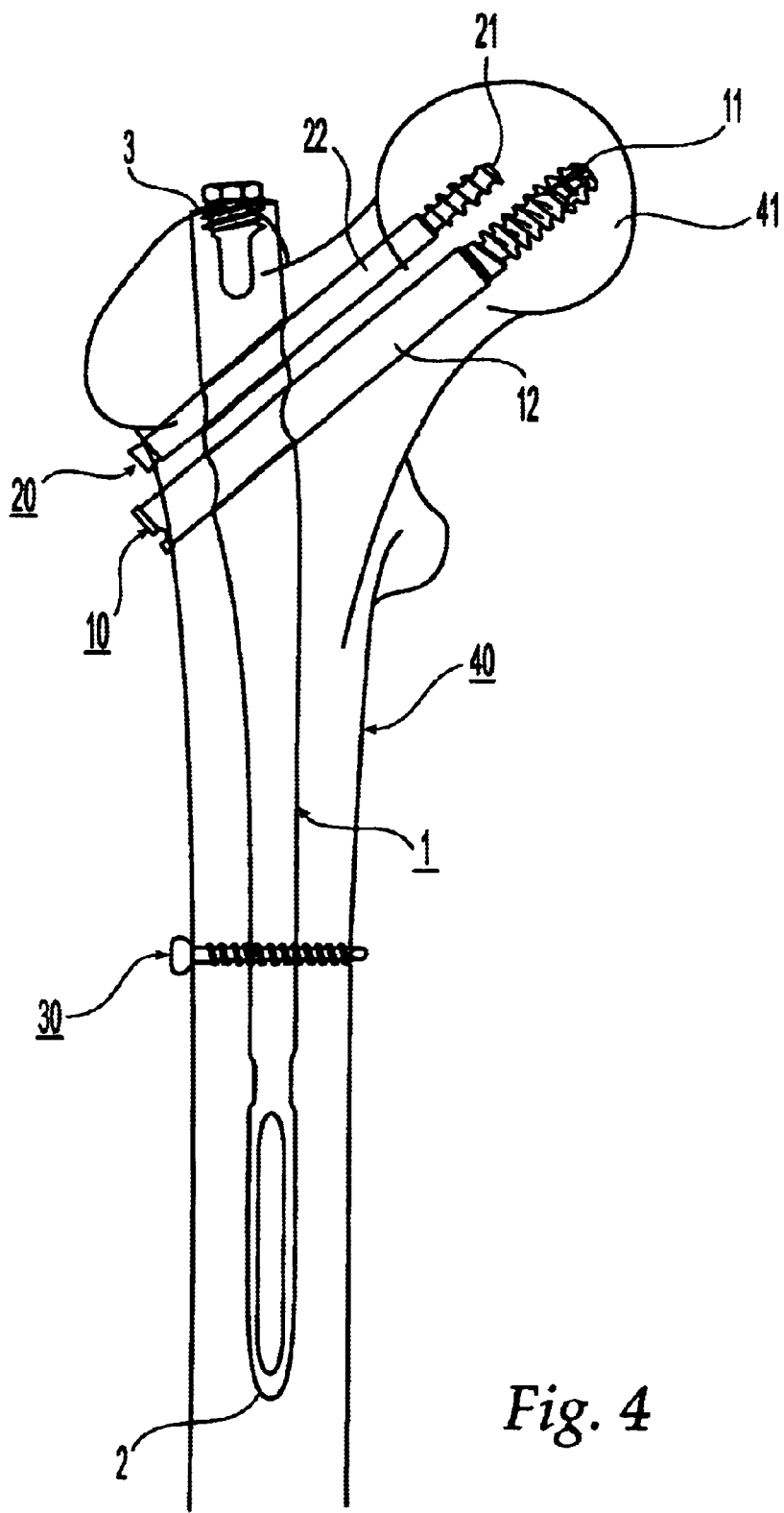
FIG. 4 is a perspective view of the fastening pin according to FIG. 1, implanted and locked in position in the femur.
Figure 7:
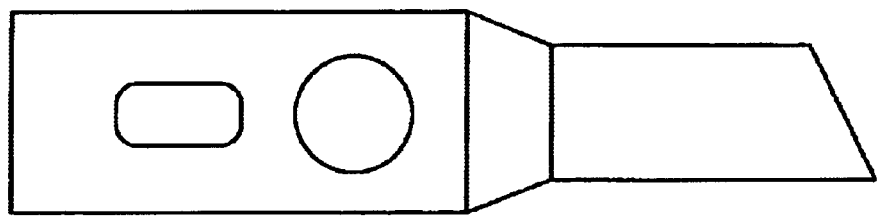
FIG. 7 is a lateral view of the proximal section of the intramedullary fastening pin with a slightly rounded slot.

As illustrated in FIGS. 1 and 4, the intramedullary fastening pin 1 is additionally provided near its distal end 2 with a third borehole 9 which horizontally intersects the longitudinal axis 4 and serves to accept a distal locking screw 30.

As shown in FIG. 4, it is desirable for the hip pin 20, consisting of shank 22 and threaded front part 21, to be 5 to 20 mm and preferably 10 to 15 mm shorter than the femoral head screw 10 which latter consists of shank 12 and threaded front part 11.

The following will briefly describe the mode of operational application of the intramedullary fastening pin according to this invention.

a) Preparation of the medullary channel of the femur;
b) Driving the fastening pin into the medullary channel;
c) Insertion of guide wires into the first proximal borehole 6 and the second proximal borehole 7;
d) Drilling the hole for hip pin 20 into the bone;
e) Insertion of hip pin 20 through the second proximal borehole 7 into the hole predrilled into the bone; once the hip pin 20 is properly seated, the femoral head is secured against any rotation during the subsequent insertion of the femoral head screw 10;
f) Drilling the hole for the femoral head screw 10 into the bone;
g) Insertion of the femoral head screw 10 through the first proximal borehole 5 and into the hole predrilled into the bone, and removal of the guide wire;
h) Drilling the hole for the distal locking provision for the intramedullary fastening pin; and insertion of a locking screw 30 in the distal third borehole 9.

While various descriptions of the present invention are described above, it should be understood that the various features can be used singularly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A fixation system for the treatment of femoral fractures, comprising an intramedullary nail, a femoral-head screw and a hip pin, wherein the intramedullary nail includes a distal end for insertion in the medullary channel, a proximal end, a longitudinal axis and, a first borehole located closer to the proximal end that intersects the longitudinal axis and is configured to accept the femoral-head screw, and the first borehole defining a center line extending at an angle α of 30° to 70° relative to the longitudinal axis; and the intramedullary nail includes a second borehole provided between the first borehole and the proximal end that intersects the longitudinal axis and is configured to accept the hip pin and is at least in part elongated into a slot with a width B and a length L>B, said length L of the slot extending in the direction of the longitudinal axis.

2. The fixation system of claim 1, wherein the first borehole is cylindrically round.

3. The fixation system of claim 1, wherein the second borehole defines a lateral entry opening that is cylindrically round and a medial exit opening that is elongated into a slot.

4. The fixation system of claim 3, wherein both the lateral entry opening and the medial exit opening of the second borehole are elongated into a slot.

5. The fixation system of claim 3, wherein the lateral entry opening of the second borehole is elongated into a slot while the medial exit opening of the second borehole is cylindrically round.

6. The fixation system of claim 1, wherein the first borehole has a diameter D and the width B of the second borehole is smaller than D.

7. The fixation system of claim 1, wherein the second borehole defines a center line that extends at an angle of between about 30° to 70° relative to the longitudinal axis.

8. The fixation system of claim 7, wherein the center line extends at an angle of between about 70° to 90° relative to the longitudinal axis.

9. The fixation system of claim 1, wherein the length L is between about 8 to 12 mm.

10. The fixation system of claim 1, wherein the width B is between about 5 to 10 mm.

11. The fixation system of claim 1, wherein the intramedullary nail further comprises a third borehole located closer to the distal end that horizontally intersects the longitudinal axis and is configured to accept a distal locking screw.

12. The fixation system of claim 1, wherein the first borehole defines a center line that extends at an angle of between about 40° to 55° relative to the longitudinal axis.

13. The fixation system of claim 1, wherein the ratio of L:B is in the range of about 1.05 to 2.00.

14. The fixation system of one of claim 1, wherein the hip pin has a length between about 5 to 20 mm and preferably 10 to 15 mm shorter than the femoral-head screw.

15. The fixation system of claim 14, wherein the diameter of the hip pin corresponds to the width B of the second borehole.

16. An intramedullary nail for the treatment of femoral fractures, comprising a distal end for insertion in the medullary channel;

a proximal end;

a longitudinal axis;

a first borehole located closer to the proximal end extending through the proximal end and intersecting the longitudinal axis and configured to accept a femoral head screw, the first borehole defining a center line extending at an angle of between about 30° to 70° relative to the longitudinal axis; and a second borehole positioned between the first borehole and the proximal end extending through the proximal end and intersecting the longitudinal axis and configured to accept a hip pin, wherein the second borehole is at least in part elongated into a slot having a width B and a length L>B, with the length L of the slot extending in the direction of the longitudinal axis; and the second borehole defines a lateral entry opening that is cylindrically round and a medial exit opening that is elongated into a slot.

17. The nail of claim 16, wherein the first borehole is cylindrically round.

18. The nail of claim 17, wherein the second borehole defines a center line that extends at an angle of between about 30° and 70° relative to the longitudinal axis.

19. An intramedullary nail for the treatment of femoral fractures, comprising a distal end for insertion in the medullary channel;

a proximal end;

a longitudinal axis;

a first borehole located closer to the proximal end extending through the proximal end and intersecting the longitudinal axis and configured to accept a femoral head screw, the first borehole defining a center line extending at an angle of between about 30° to 70° relative to the longitudinal axis; and a second borehole positioned between the first borehole and the proximal end extending through the proximal end and intersecting the longitudinal axis and configured to accept a hip pin, wherein the second borehole is at least in part elongated into a slot having a width B and a length L>B, with the length L of the slot extending in the direction of the longitudinal axis; and the second borehole defines a lateral entry opening that is elongated into a slot and a medial exit opening that is cylindrically round.

* * * * *